United States Patent [19]

Nüsslein et al.

[11] 4,005,213
[45] Jan. 25, 1977

[54] 2,5-SUBSTITUTED-1,3,4-THIADIAZOLES AS FUNGICIDES

[75] Inventors: Ludwig Nüsslein; Ernst Albrecht Pieroh; Kurt Röder, all of Berlin, Germany

[73] Assignee: Schering Aktiengesellschaft, Berlin, Germany

[22] Filed: Dec. 11, 1974

[21] Appl. No.: 531,901

Related U.S. Application Data

[63] Continuation-in-part of Ser. No. 298,274, Oct. 17, 1972, abandoned, which is a continuation-in-part of Ser. No. 883,253, Dec. 8, 1969, abandoned.

[30] Foreign Application Priority Data

Dec. 21, 1968 Germany .......................... 1817069

[52] U.S. Cl. .............................. 424/270; 424/DIG. 8
[51] Int. Cl.² ........................ A01N 9/12; A01N 9/20
[58] Field of Search ................................. 424/270

[56] References Cited

UNITED STATES PATENTS

| | | | |
|---|---|---|---|
| 3,562,284 | 2/1971 | Newman et al. | 260/302 |
| 3,576,843 | 4/1971 | Model et al. | 424/313 |
| 3,692,794 | 9/1972 | Rosen | 260/302 |

OTHER PUBLICATIONS

Chemical Abstracts, vol. 73 (1970), p. 45516w (Abstract of German Offen. No. 1,817,069).

*Primary Examiner*—V. D. Turner
*Attorney, Agent, or Firm*—Joseph F. Padlon

[57] ABSTRACT

The specification discloses the preparation and use, as fungicides and nematocides, of 2,5-substituted-1,3,4-thiadiazoles having the structure:

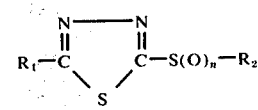

wherein $R_1$ is a lower haloalkyl and $R_2$ is an aliphatic hydrocarbon.

The instant invention is directed to methods for the control of fungi and nematodes in soil and seeds and to compounds useful in such methods. In another aspect, the invention is concerned with the preparation of 2,5-substituted-1,3,4-thiadiazoles and formulation for agricultural use in which such compounds are the principal biocidal ingredient.

7 Claims, No Drawings

2,5-SUBSTITUTED-1,3,4-THIADIAZOLES AS FUNGICIDES

This is a continuation-in-part of application Ser. No. 298,274 filed Oct. 17, 1972, now abandoned which is a continuation-in-part of application Ser. No. 883,253 filed Dec. 8, 1969, now abandoned.

SUMMARY OF THE INVENTION

It is an object of the present invention to provide new thiadiazole compounds which are effective in the control of fungi and nematodes. Another object of the invention is to provide new 2,5-substituted-1,3,4-thiadiazoles which are effective in the treatment of seeds, plants, and herbs for the purpose of protecting the seeds, plants and herbs against infestation by fungi and nematodes and further to control or eliminate already existing infestation. Another aspect of the invention is concerned with the preparation and provision of agricultural formulations containing these compounds as active ingredients.

Other embodiments of the invention provide methods and processes for the control of fungi and nematodes in seeds and crop plants by treatment thereof with the compounds of this invention or formulations of such compounds.

THE INVENTION

The above and other related objects are achieved through the use of compounds having the formula

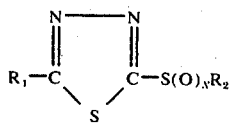

wherein $R_1$ is lower haloalkyl group and $R_2$ is an aliphatic hydrocarbon and $n$ is an integer of 1 or 2. The term lower alkyl is intended to include alkyl groups having from 1 to 7 carbon atoms which can have from 1 to 3 halo substituents. Illustrative groups include chloromethyl, dichloromethyl, tricholoromethyl and the corresponding bromo and fluoro compounds.

Suitable aliphatic radicals are those containing from 1 to 8 carbon atoms in straight or branched chain structures. Preferred groups include alkyl groups of 1 to 8 carbons such as methyl, ethyl, propyl, isopropyl, butyl, pentyl, hexyl, heptyl, and octyl and the like.

Of the compounds included in the above general formula it must be understood that lower alkyl radicals containing up to 7 carbon atoms which may be halogenated, e.g., mono- or multi-fluorinated, -chlorinated or -brominated are especially useful. Compounds in which $R_1$ is mono-, di- or tri-halogen methyl radicals, such as monochloromethyl, dichloromethyl, trichloromethyl, dibromomethyl or trifluoromethyl are outstanding.

The aliphatic hydrocarbon radical $R_2$ preferably contains from 1 to 8 carbon atoms, in particular straight-chain or branched alkyl radicals, for example methyl, ethyl, propyl, isopropyl, butyl, pentyl, hexyl, heptyl and octyl radicals, etc.

Illustrative compounds include:
2-trifluoromethyl-5-methylsulfonyl-1,3,4-thiadiazole,
2-dichloromethyl-5-methylsulfinyl-1,3,4-thiadiazole,
2-trichloromethyl-5-methylsulfinyl-1,3,4-thiadiazole,
2-dichloromethyl-5-methylsulfonyl-1,3,4-thiadiazole,
2-trichloromethyl-5-methylsulfonyl-1,3,4-thiadiazole,
2-trichloromethyl-5-propylsulfinyl-1,3,4-thiadiazole,
2-dichloromethyl-5-propylsulfonyl-1,3,4-thiadiazole,
2-dichloromethyl-5-ethylsulfinyl-1,3,4-thiadiazole,
2-trifluoromethyl-5-ethylsulfonyl-1,3,4-thiadiazole,
2-trifluoromethyl-5-methylsulfinyl-1,3,4-thiadiazole,
2-trifluoromethyl-5-ethylsulfinyl-1,3,4-thiadiazole,
2-trifluoromethyl-5-isopropylsilfinyl-1,3,4-thiadiazole, and
2-trifluoromethyl-5-isopropylsulfonyl-1,3,4-thiadiazole.

These compounds have been found to have substantial and superior activity against fungi infesting soil, seed and plants, particularly against Pythium, Rhizoctonia, Fusarium, Tilletia, Botryis, Helminthosporium, Venturia, Plasmopara, and other fungi.

The compounds of this invention can be formulated into admixture with various ingredients to form agricultural compositions which can be conveniently applied to the infested area or to soil, seeds or plants to be protected. In general the active ingredient is used in an effective amount, i.e., an amount sufficient to substantially prevent infestation or to substantially destroy or prevent further growth of the infesting organisms in cases of pre-existing infestation. For the sake of convenience of expression the term fungi controlling has been adapted to describe the characteristic of inhibiting both future infestation and continued growth of existing infestations. Since the disclosed compounds are substantially non-toxic to animals and plants at effective levels of application they can be on seeds and plants with little damage to the crops themselves or to warm blooded animals feeding on the crops. Accordingly one of the unusual aspects of these compounds which in large measure contributes to the successful use thereof in methods for the protection of plants and crops is the excellent tolerance which is exhibited by the plants to the compounds. Safety with respect to animals is indicated by an acute oral toxicity (LD50) of 717 mg per kg in rats for a representative compound, 2-trichloromethyl-5-methylsulfonyl-1,3,4-thiadiazole.

In addition to outstanding fungicidal activity these compounds can be employed in compositions and methods for the control of other agricultural pests, specifically bacteria and nematodes, and such aspects of use are an inherent aspect of their use.

The compounds can be used in agriculture and horticulture for general treatment of soil, seed, or planted furrows. The action is directed not only to damaging fungi which attack from the soil, but also to those which are transmitted by seed and parasites on above-ground plant parts. Surprisingly, the fungicidal ingredients according to the invention show, in part, systemic properties. With the application of the invention, soil-inhabiting nematodes are controlled and bacteria destroyed.

The active ingredients may be used alone or mixed with one another, or if desired, with other plant protecting pest control agents, e.g. with insecticides, if the simultaneous control of these or other pests is desired.

Application is effected expediently as powder, scatter material, granules, solution, emulsion or suspension, or as aerosols with the addition of solid or liquid diluents or vehicles and possibly of adhesive, wetting, emulsifying and/or dispersing aids well known in the agricultural arts.

Illustrative liquid vehicles include water, mineral oils or other organic solvents, such as xylene, chlorobenzene, chloroform, 1.3-dichloroprene, cyclohexanone, ether, acetic ester, dimethyl formamide, dimethyl sulfoxide, ethylene dibromide and 1,2-dichloro-3-bromopropane and the like.

Suitable solid vehicles include lime, clays such as attacloy, kaolin, talcum, and natural or snythetic silica, and the like.

Surface-active substances suitable for use in the invention include salts of the lignin-sulfonic acids, salts of alkylated benzene-sulfonic acids, sulfonated acid amides and their salts, polyethoxylated amines and alcohols. If the active substances are to be used for seed disinfection, dyes, such as new fuchsine, etc., may be admised to give the disinfected seed a clearly visible coloration.

The proportion of carrier and active substance or substances in the formulation is not narrowly critical provided a fungi-controlling amount of active agent is provided. The exact amount of active ingredient used depends mainly on the concentration in which the agents are to be used for soil or seed treatment. In general effective formulations contain from about 0.1 to 80 percent by weight, preferably 10 to 50 percent by weight, of the active ingredient and about 99 to 20 percent by weight of the liquid or solid vehicles. Optionally the formulation can contain up to 20 percent by weight of a surface-active substance. Suitable formulations can be prepared by means known in the art such as by grinding or mixing processes. The term carrier is used herein to describe such vehicles and other adjuvents such as surfactants and diluents as are commonly used in the formulation of agricultural chemicals. Remarkably it has been found that these active substances are excellently suitable for preparation of dry disinfectant compositions of low active ingredient content.

The formulations can be applied to the seed in the usual manner either before sowing or during sowing in the furrow (so-called tilling-in). For treatment of the soil itself, the agents are expediently introduced in the upper soil layers to a depth of about 20 cm. e.g. by hoeing in.

The compounds of this invention may be produced, for example, by the action of oxidizing agents on corresponding 5-mercapto-1,3,4-thiadiazoles of the general formula:

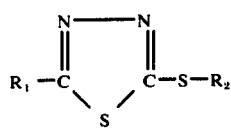

wherein the radicals $R_1$ and $R_2$ are as previously defined.

Compounds in which $n$ is 1 can be prepared with organic hydroperoxides, such as tertiary butyl hydroperoxide, or m-chloroperbenzoic acid, and the like, or inorganic reagents such as hydrogen peroxice, sodium-m-periodate, and the like. Advantageously the reaction is carried out using two oxidation equivalents of the oxidizing agent per mole of the mercapto compound at temperatures of about 0° to about 40° C.

Compounds in which $n$ is 2 can be prepared using the oxidizing agents already named or inorganic reagents such as potassium permananate, chromic acid or their salts, or nitric acid, in the temperature range from about 0° to 120° C. In this reaction four of the oxidizing agent per mole of mercapto are used, that is, twice as much as is required for the above described reaction.

The reaction can be carried out in a media comprising organic solvents such as acetic acid, ether, dioxane, ketones, acetone or others, and either inidivdually or in mixture with water.

The following examples explain the production of the compounds:

a. 24.9 g of 2-trichloromethyl-5-methylmercapto-1,3,4-thiadiazole are dissolved in 200 ml of glacial acetic acid, 11.3 g of a 30% hydrogen peroxide being added drop by drop and left standing over night. The mixture is then concentrated under vacuum, the residue taken up in methylene chloride, the remaining acetic acid is removed with dilute soda solution, the resultant residue is dried in the organic phase, concentrated and recrystallized from a small amount of isopropyl ether.

Yield: 23.4 g or 88% of the theory of 2-trichloromethyl-5-methylsulfinyl-1,3,4-thiadiazole, m.p. 89°–90° C.

b. Into a solution of 107.6 g of 2-dichloromethyl-5-methyl-mercapto-1,3,4-thiadiazole in 750 ml of glacial acetic acid and 300 ml of water slowly put 105.5 g of potassium permanganate, by portions. During charging, the temperature is maintained at 10° C. while vigorously agitating. Let react at the same temperature for another 30 minutes, then add 2.5 liter of water, and reduce the precipitated $MnO_2$ between 0° and 5° C. with a solution consisting of 95 g of sodium metabisulfite in 400 ml of water. When almost the entire amount has been dropped in, the reduction is completed with decoloration. Suction off the precipitated substance, wash with water, and recrystallize from about 170 ml of isopropanol.

Yield: 92 g corresponding to 74% of the theory of 2-dichloromethyl-5-methyl-sulfonyl-1,3,4-thiadiazole, m.p. 75° C.

c. Into a solution of 36.75 g of 2-dichloromethyl-5-ethyl-mercapto-1,3,4-thiadiazole in 200 ml of chloroform slowly charge, while stirring and cooling with 28.5 g of m-chloroperbenzoic acid. Let react for another hour, extract the m-chlorobenzoic acid with dilute soda solution, wash with water, and dry over magnesium sulfate. After evaporation of the solvent, recrystallize, from little isopropyl ether.

Yield: 33 g corresponding to 88% of the theory of 2-dichloromethyl-5-ethyl-sulfonyl-1,3,4-thiadiazole, m.p. 75° C.

Additional compounds according to the invention are listed in the following table.

| Compound No. | Name of Compound | Physical Constant |
|---|---|---|
| 1 | 2-trifluoromethyl-5-methyl-sulfonyl-1,3,4-thiadiazole | m.p. 88° C. |
| 2 | 2-chloromethyl-5-methyl-sulfinyl-1,3,4-thiadiazole | $n_D^{20} = 1.5911$ |
| 3 | 2-dichloromethyl-5-methyl-sulfinyl-1,3,4-thiadiazole | m.p. 86° C. |
| 4 | 2-dichloromethyl-5-ethyl-sulfinyl 1,3,4-thiadiazole | m.p. 61° C. |
| 5 | 2-dichloromethyl-5-propyl-sulfinyl-1,3,4-thiadiazole | $n_D^{20} = 1.5703$ |

-continued

| Compound No. | Name of Compound | Physical Constant |
|---|---|---|
| 6 | 2-dichloromethyl-5-isopropyl-sulfinyl-1,3,4-thiadiazole | m.p. 60° C. |
| 7 | 2-dichloromethyl-5-amylsulfinyl 1,3,4-thiadiazole | $n_D^{20}=1.5541$ |
| 8 | 2-trichloromethyl-5-methyl-sulfinyl-1,3,4-thiadiazole | m.p. 89° C. |
| 9 | 2-trichloromethyl-5-ethyl-sulfinyl-1,3,4-thiadiazole | $n_D^{20}=1.5830$ |
| 10 | 2-trichloromethyl-5-propyl-sulfinyl-1,3,4-thiadiazole | $n_D^{20}=1.5740$ |
| 11 | 2-trichloromethyl-5-isopropyl-sulfinyl-1,3,4-thiadiazole | $n_D^{20}=1.5743$ |
| 12 | 2-trichloromethyl-5-butyl-sulfinyl-1,3,4-thiadiazole | $n_D^{20}=1.5652$ |
| 13 | 2-trichloromethyl-5-heptyl-sulfinyl-1,3,4-thiadiazole | $n_D^{20}=1.5391$ |
| 14 | 2-trichloromethyl-5-octyl-sulfinyl-1,3,4-thiadiazole | $n_D^{20}=1.5380$ |
| 15 | 2-chloromethyl-5-methyl-sulfonyl-1,3,4-thiadiazole | m.p. 50° C. |
| 16 | 2-chloromethyl-5-isopropyl-sulfonyl-1,3,4-thiadiazole | $n_D^{20}=1.5482$ |
| 17 | 2-dichloromethyl-5-methyl-sulfonyl-1,3,4-thiadiazole | m.p. 75° C. |
| 18 | 2-dichloromethyl-5-ethyl-sulfonyl-1,3,4-thiadiazole | m.p. 76° C. |
| 19 | 2-dichloromethyl-5-propyl-sulfonyl-1,3,4-thiadiazole | $n_D^{20}=1.5554$ |
| 20 | 2-dochloromethyl-5-isopropyl-sulfonyl-1,3,4-thiadiazole | m.p. 58° C. |
| 21 | 2-trichloromethyl-5-methyl-sulfonyl-1,3,4-thiadiazole | m.p. 123° C. |
| 22 | 2-trichloromethyl-5-ethyl-sulfonyl-1,3,4-thiadiazole | $n_D^{20}=1.5593$ |
| 23 | 2-trichloromethyl-5-propyl-sulfonyl-1,3,4-thiadiazole | m.p. 78° C. |
| 24 | 2-trichloromethyl-5-isopropyl-sulfonyl-1,3,4-thiadiazole | m.p. 98° C. |
| 25 | 2-trichloromethyl-5-butyl-sulfonyl-1,3,4-thiadiazole | m.p. 77° C. |
| 26 | 2-trichloromethyl-5-amylsulfonyl-1,3,4-thiadiazole | m.p. 50° C. |
| 27 | 2-trichloromethyl-5-hexyl-sulfonyl-1,3,4-thiadiazole | m.p. 47° C. |
| 28 | 2-trichloromethyl-5-hepty-sulfonyl-1,3,4-thiadiazole | m.p. 54° C. |
| 29 | 2-trichloromethyl-5-octyl-sulfonyl-1,3,4-thiadiazole | m.p. 50° C. |
| 30 | 2-bromomethyl-5-methyl-sulfonyl-1,3,4-thiadiazole | $n_D^{20}=1.5993$ |
| 31 | 2-bromomethyl-5-ethyl-sulfonyl-1,3,4-thiadiazole | m.p. 99° C. |
| 32 | 2-dibromomethyl-5-methyl-sulfonyl-1,3,4-thiadiazole | m.p. 113° C. |
| 33 | 2-fluoromethyl-5-methyl-sulfinyl-1,3,4-thiadiazole | m.p. 45° C. |
| 34 | 2-fluoromethyl-5-methyl-sulfonyl-1,3,4-thiadiazole | m.p. 64° C. |
| 35 | 2-trifluoromethyl-5-methyl-sulfinyl-1,3,4-thiadiazole | m.p. 53° C. |
| 36 | 2-trifluoromethyl-5-ethyl-sulfinyl-1,3,4-thiadiazole | $n_D^{20}=1.4897$ |
| 37 | 2-trifluoromethyl-5-isobutyl-sulfinyl-1,3,4-thiadiazole | m.p. 54° C. |
| 38 | 2-trifluoromethyl-5-pentyl-sulfinyl-1,3,4-thiadiazole | $n_D^{20}=1.4801$ |
| 39 | 2-trifluoromethyl-5-hexyl-sulfinyl-1,3,4-thiadiazole | $n_D^{20}=1.4790$ |
| 40 | 2-trifluoromethyl-5-ethyl-sulfonyl-1,3,4-thiadiazole | b.p. 79° C. 0.05 Torr |
| 41 | 2-trifluoromethyl-5-isopropyl-sulfonyl-1,3,4-thiadiazole | m.p. 77° C. |
| 42 | 2-trifluoromethyl-5-isobutyl-sulfonyl-1,3,4-thiadiazole | m.p. 41° C. |
| 43 | 2-trifluoromethyl-5-hexyl-sulfonyl-1,3,4-thiadiazole | m.p. 47° C. |
| 44 | 2-trifluoromethyl-5-heptyl-sulfonyl-1,3,4-thiadiazole | m.p. 64° C. |
| 45 | 2-pentafluoroethyl-5-methyl-sulfonyl-1,3,4-thiadiazole | m.p. 66° C. |
| 46 | 2-heptafluoropropyl-5-methyl-sulfonyl-1,3,4-thiadiazole | m.p. 71° C. |
| 47 | 2-(1,1-dichloroethyl)-5-methyl-sulfonyl-1,3,4-thiadiazole | m.p. 63° C. |
| 48 | 2-(1-chloropropyl)-5-methyl-sulfinyl-1,3,4-thiadiazole | $n_D^{20}=1.5661$ |
| 49 | 2-(1-chloropropyl)-5-methyl-sulfonyl-1,3,4-thiadiazole | m.p. 56° C. |
| 50 | 2-(1-bromethyl)-5-methyl-sulfonyl-1,3,4-thiadiazole | $n_D^{20}=1.5730$ |
| 51 | 2-(1-bromisobutyl)-5-methyl-sulfonyl-1,3,4-thiadiazole | $n_D^{20}=1.5529$ |
| 52 | 2-(1-bromopentyl)-5-methyl-sulfonyl-1,3,4-thiadiazole | $n_D^{20}=1.5443$ |
| 53 | 2-(1-bromisopentyl)-5-methyl-sulfonyl-1,3,4-thiadiazole | $n_D^{20}=1.5401$ |
| 54 | 2-chlorodifluoromethyl-5-methyl-sulfonyl-1,3,4-thiadiazole | m.p. 56° C. |
| 55 | 2-chlorodifluoromethyl-5-methyl-sulfinyl-1,3,4-thiadiazole | m.p. 52° C. |
| 56 | 2-trifluoromethyl-5-propyl-sulfinyl-1,3,4-thiadiazole | b.p. 83° C./0.15 Torr |
| 57 | 2-trifluoromethyl-5-propyl-sulfonyl-1,3,4-thiadiazole | b.p. 136° C/18 Torr |
| 58 | 2-trifluoromethyl-5-isopropyl-sulfinyl-1,3,4-thiadiazole | b.p. 58–61° C/0.7 Torr |

The compounds are soluble in chlorinated hydrocarbons, such as chloroform, 1,3-dichloroprene, etc., ethers such as dioxane and others, ketones such as acetone, cyclohexanone, etc., esters such as acetic ester, etc., acids such as acetic acid etc., and dimethylformamide as well as dimethylsulfoxide, etc.

The following examples serve to elucidate and establish the effectiveness of the active substances according to the invention.

EXAMPLE 1

Limit concentrations of the soil-fungicidal effectiveness at homogeneous mixture of the products with the infested soil. Basic condition in the evaluation are a sound root formation without fungus necroses and germination of the seed of at least 90% compared with the result obtained in steamed soil. Per concentration there were seeded 25 grains of peas of the variety "Miracle of Kelvedon" (marrow pea) without a waiting period. the cultivation time in the tests was 20 to 23 days at a temperature of 22°–25° C. Four commercial products were included in the test series.

*Pythium ultimum:* Steamed compost soil was inoculated with mycelium of *Pythium ultimum*

*Rhizoctonia solani:* Steamed compost soil was inoculated with mycelium of *Rhizoctoniz solani*.

Limit concentrations of the fungicidal effectiveness (mg of active substance per liter of soil) determined thus far.

| Compound No. | Pythium ultimum | Rhizoctonia solani |
|---|---|---|
| 1 | 10 mg | 25 mg |
| 2 | 30 mg | 50 mg |
| 3 | 10 mg | 30 mg |
| 4 | 100 mg | 20 mg |
| 5 | 100 mg | 20 mg |
| 6 | over 200 mg | 50 mg |
| 7 | over 200 mg | 50 mg |
| 8 | 20 mg | 10 mg |
| 9 | 200 mg | 10 mg |
| 10 | 100 mg | 20 mg |
| 11 | over 200 mg | 50 mg |
| 12 | 200 mg | 50 mg |
| 13 | over 200 mg | 200 mg |
| 14 | over 200 mg | 100 mg |
| 15 | 10 mg | 100 mg |
| 16 | 150 mg | 200 mg |
| 17 | 10 mg | 20 mg |
| 18 | over 200 mg | 100 mg |
| 19 | 100 mg | 50 mg |
| 20 | 200 mg | 50 mg |
| 21 | 40 mg | 10 mg |

-continued

| Compound No. | Pythium ultimum | Rhizoctonia solani |
|---|---|---|
| 22 | 50 mg | 50 mg |
| 23 | 150 mg | 30 mg |
| 24 | 150 mg | 30 mg |
| 25 | over 200 mg | 25 mg |
| 26 | over 200 mg | 25 mg |
| 27 | over 200 mg | 25 mg |
| 28 | over 200 mg | 200 mg |
| 29 | over 200 mg | over 200 mg |
| 30 | 20 mg | 150 mg |
| 31 | 50 mg | over 200 mg |
| 32 | 20 mg | 50 mg |
| 33 | 50 mg | 20 mg |
| 34 | 50 mg | 30 mg |
| 35 | 10 mg | 20 mg |
| 36 | 10 mg | 20 mg |
| 37 | 30 mg | 100 mg |
| 38 | 100 mg | 40 mg |
| 39 | 100 mg | 40 mg |
| 40 | 10 mg | 20 mg |
| 41 | 10 mg | 20 mg |
| 42 | 20 mg | 100 mg |
| 43 | over 100 mg | 50 mg |
| 44 | over 100 mg | 50 mg |
| 45 | 100 mg | over 100 mg |
| 46 | 100 mg | 100 mg |
| 47 | 80 mg | 50 mg |
| 48 | over 100 mg | 100 mg |
| 49 | 100 mg | 50 mg |
| 50 | 40 mg | 100 mg |
| 51 | over 100 mg | 50 mg |
| 52 | no effect | 100 mg |
| 53 | no effect | 100 mg |
| 54 | 10 mg | 20 mg |
| 55 | 10 mg | 10 mg |

Comparative agents

| | | |
|---|---|---|
| 5-ethoxy-3-trichloro-methyl-1,2,4-thiadiazole | 20 mg | insufficient effect |
| 1,4-dichloro-2,5 dimethoxy-benzene | insufficient effect | 30 mg |
| Pentachloronitrobenzene | insufficient effect | 75 mg |
| N-(trichloromethylthio)-cyclohex-4-ene-1,2-dicarboximide | 300 mg | 300 mg |

The superiority of the compounds according to the invention over the known fungicides is evident from the test data above given.

EXAMPLE 2

Steamed compost soil was inoculated with mycelium of *Pythium ultimum*. After a homogeneous mixture of the products with the infested soil, the products were in the form of 20% powder preparations, the seeding of 25 grains of marrow peas of the variety Miracle of Kelvedon per concentration was effected without a waiting period in clay dishes holding 1 liter of soil. The following table lists the number of germinated sound peas, the weight of the fresh plant, and a root evaluation after a cultivation period of 3 weeks at 22°–25° C.

Root evaluation:
4 = white roots, without fungus necroses
3 = white roots, slight fungus necroses
2 = brown roots, more intense fungus necroses
1 = severe fungus necroses, roots rotted

| Compound No. | mg of active ingr. per liter of soil | Number of sound peas after 3 wks. | Weight of fresh plant (g) | Root evaluation (1–4) |
|---|---|---|---|---|
| 1 | 10 mg | 25 | 20 g | 4 |
| | 20 mg | 22 | 19 g | 4 |
| | 30 mg | 23 | 19 g | 4 |
| 3 | 10 mg | 24 | 22 g | 4 |
| | 20 mg | 24 | 24 g | 4 |
| | 30 mg | 25 | 22 g | 4 |
| 8 | 10 mg | 19 | 12 g | 1 |
| | 20 mg | 24 | 22 g | 4 |
| | 30 mg | 25 | 22 g | 4 |
| 15 | 10 mg | 22 | 20 g | 4 |
| | 20 mg | 23 | 20 g | 4 |
| | 30 mg | 24 | 20 g | 4 |
| 17 | 10 mg | 23 | 24 g | 4 |
| | 20 mg | 24 | 22 g | 4 |
| | 30 mg | 24 | 26 g | 4 |
| 30 | 10 mg | 21 | 18 g | 1 |
| | 20 mg | 24 | 24 g | 4 |
| | 30 mg | 22 | 18 g | 4 |
| Comparative Agents | | | | |
| 5-ethoxy-3-tri-chloro-methyl-1,2,4-thiadiazole | 10 mg | 12 | 10 g | 1 |
| | 20 mg | 21 | 16 g | 4 |
| | 30 mg | 19 | 14 g | 4 |
| 1,4-dichloro-2,5-dimethoxy-benzene | 200 mg | 2 | 1 g | 1 |
| N-(trichloro-methyl) thio)-cyclohex-4-ene-1,2-dicarboximide | 200 mg | 13 | 6 g | 1 |
| Zinc ethylene-bis-dithiocarbamate | 200 mg | 14 | 7 g | 1 |
| Steamed soil | — | 20 | 16 g | 4 |
| Untreated soil | — | 0 | 0 g | — |

It follows from the findings at hand that even the 1,2,4-thiadiazole derivative known to have specific Pythium action does not exceed the action of the compounds according to the invention against this fungus, but is, on the contrary, in part somewhat less effective than these.

EXAMPLE 3

Steamed compost soil was inoculated with mycelium of *Rhizoctonia solani*. After homogeneous mixture of the products with the infested soil, the products were present in the form of 20% powder preparations, the seeding of 25 grains of marrow peas of the variety Miracle of Kelvedon per concentration was effected without waiting period in clay dishes holding 1 liter of soil. The table lists the number of germinated sound peas, the weight of the fresh plant, and a root evaluation after a cultivation period of 3 weeks at 22°–25° C.

| Compound No. | mg of active ingr. per liter of soil | Number of sound peas after 3 wks. | Weight of fresh plant (g) | Root evaluation (1–4) |
|---|---|---|---|---|
| 3 | 10 mg | 0 | 0 g | — |
|  | 20 mg | 2 | 2 g | 1 |
|  | 30 mg | 22 | 21 g | 4 |
| 8 | 10 mg | 21 | 17 g | 4 |
|  | 20 mg | 24 | 17 g | 4 |
|  | 30 mg | 24 | 17 g | 4 |
| 9 | 10 mg | 22 | 18 g | 4 |
|  | 20 mg | 22 | 16 g | 4 |
|  | 30 mg | 23 | 17 g | 4 |
| 17 | 10 mg | 0 | 0 g | — |
|  | 20 mg | 23 | 14 g | 4 |
|  | 30 mg | 22 | 14 g | 4 |
| 21 | 10 mg | 17 | 11 g | 4 |
|  | 20 mg | 24 | 17 g | 4 |
|  | 30 mg | 24 | 17 g | 4 |
| 23 | 10 mg | 13 | 9 g | 1 |
|  | 20 mg | 21 | 17 g | 3 |
|  | 30 mg | 24 | 20 g | 4 |
| Comparative Agents | | | | |
| 1,4-dichloro-2,5-dimethoxy-benzene | 10 mg | 0 | 0 g | — |
|  | 20 mg | 0 | 0 g | — |
|  | 30 mg | 21 | 18 g | 4 |
|  | 40 mg | 22 | 18 g | 4 |
| Pentachloronitro benzene | 50 mg | 4 | 4 g | 1 |
|  | 100 mg | 25 | 15 g | 4 |
| Steamed soil | — | 20 | 17 g | 4 |
| Untreated soil | — | 0 | 0 g | — |

The above test results prove the superior action of the compounds according to the invention against Rhizoctonia in comparison with commercial products.

EXAMPLE 4

Comparison of the fungistatic and fungicidal action on *Pythium ultimum* when using preparations with varying active ingredient percentages on siliceous clay. Steamed compost soil was inoculated with mycelium of *Pythium ultimum*. After forming a homogeneous mixture of the products with the infested soil, the products were present in the form of 20% powder preparations, the seeding of 25 grains of marrow peas of the variety Miracle of Kelvedon per concentration in clay dishes holding 1 liter of soil followed without a waiting period. In the table is stated the number of germinated sound peas, the weight of the fresh plant, and a root evaluation after a cultivation period of 3 weeks at 22°–25° C.

| Compound No. 17 | mg of active ingr. per liter of soil | Number of sound peas after 3 wks. | Weight of fresh plant (g) | Root evaluation (1–4) |
|---|---|---|---|---|
| 20% formulation | 6 mg | 22 | 17 | 2 |
|  | 10 mg | 24 | 16 | 4 |
| 10% formulation | 6 mg | 24 | 15 | 1 |
|  | 10 mg | 22 | 24 | 4 |
| 5% formulation | 6 mg | 12 | 9 | 1 |
|  | 10 mg | 24 | 20 | 4 |
| Steamed soil | — | 24 | 20 | 4 |
| Untreated soil | — | 0 | 0 | — |

This experiment shows that with concentrations of 6 mg of active ingredient per liter of woil, considerable fungistatic effects are attained. At a dosage of 10 mg of active ingredient per liter of soil, the action of the tested formulations is optimal.

EXAMPLE 5

Steamed compost soil was inoculated with a spore suspension of *Fusarium oxysporum* f. callistephi. After homogeneous mixture of the products with the infested soil, the products were present as 20% powder preparations, and after a waiting period of 8 days, there were set out per concentration four seedlings of *Callistephus chinensis*, master aster "Sun Ray" as host plants. The following table states the number of attacked plants after 3 weeks.

| Compound No. | mg of active ingr. per liter of soil | No. of attacked plants after 3 weeks |
|---|---|---|
| 3 | 50 mg | 0 |
|  | 100 mg | 0 |
| 8 | 50 mg | 0 |
|  | 100 mg | 0 |
| 9 | 50 mg | 0 |
|  | 100 mg | 0 |
| 17 | 50 mg | 0 |
|  | 100 mg | 0 |
| 19 | 50 mg | 0 |
|  | 100 mg | 0 |

-continued

| Compound No. | mg of active ingr. per liter of soil | No. of attacked plants after 3 weeks |
|---|---|---|
| 21 | 50 mg | 0 |
|  | 100 mg | 0 |
| 22 | 50 mg | 0 |
|  | 100 mg | 0 |
| 25 | 50 mg | 0 |
|  | 100 mg | 0 |
| Comparative Agents |  |  |
| N-(trichloromethyl-thio)-cyclohex-4-3n3-1,2-dicarboximide | 50 mg | 4 |
|  | 100 mg | 4 |
|  | 200 mg | 4 |
| 5-ethoxy-3-trichloromethyl-1,2,4-thiadiazole | 50 mg | 4 |
|  | 100 mg | 4 |
|  | 200 mg | 4 |
| 1,4-dichloro-2,5-dimethoxy-benzene | 50 mg | 4 |
|  | 100 mg | 4 |
|  | 200 mg | 4 |
| Steamed soil |  | 0 |
| Untreated soil |  | 4 |

This experiment, too, shows the superiority of the compounds according to the invention over commercial fingicides.

EXAMPLE 6

Cotton seeds disinfected with 10% formulations were seeded in normal compost soil (Damping-off Fungi), 25 grains per concentration. After a cultivation time of 15 days at 22°–25° C., the number of germinated sound cotton seedlings and their weight as fresh plants were determined.

| Compound No. | Active ingr. per kg of seed | Sound plants in % | Weight of fresh plant |
|---|---|---|---|
| 3 | 100 mg | 100% | 29 g |
| 8 | 100 mg | 96% | 29 g |
| 17 | 100 mg | 100% | 23 g |
| 21 | 100 mg | 100% | 33 g |
| Steamed soil, seed without disinfection |  | 100% | 27 g |
| Untreated soil, seed without disinfection |  | 50% | 14.5 g |

From this experiment, the excellent effectiveness of the compounds according to the invention when used as disinfectants for cotton seed is evident.

EXAMPLE 7

The fungicidal action of the agents according to the invention was tested in artificial nutrient media against plant-pathogenic fungi in Petri dishes (agar test). The procedure was to sterilize the medium consisting of 2% malt extract and 1.5% agar-agar powder. Before the solidification of the medium, the active substances were added to it, mixing thoroughly, so that the medium received 10 parts of active substance per million (ppm). After the solidification of the medium, the latter was inoculated with a platinum dropper which contained 100 spores each of the fungi to be tested, and after 5 days at 22° C., an evaluation was made by measuring the diameter of the colonies in mm.

| Comp. No. | Aspergilus niger | Botrytis cinerea | Colletotrichum gloeosporioides | Helminthosporium sativum | Stemphylium ilicis |
|---|---|---|---|---|---|
| 1 | 0 | 0 | 0 | 0 | 0 |
| 3 | 50 | 36 | 0 | 0 | 0 |
| 7 | 0 | 22 | 0 | 0 | 0 |
| 8 | 0 | 0 | 0 | 0 | 0 |
| 9 | 0 | 0 | 0 | 0 | 0 |
| 10 | 0 | 0 | 0 | 0 | 0 |
| 12 | 0 | 0 | 0 | 0 | 0 |
| 13 | 0 | 13 | 0 | 0 | 0 |
| 17 | 0 | 0 | 0 | 0 | 0 |
| 18 | 0 | 13 | 41 | 0 | 0 |
| 19 | 0 | 0 | 0 | 0 | 0 |
| 21 | 0 | 0 | 0 | 0 | 0 |
| 22 | 0 | 0 | 0 | 0 | 0 |
| 23 | 0 | 0 | 0 | 0 | 0 |
| 24 | 0 | 0 | 0 | 0 | 0 |
| 25 | 0 | 0 | 0 | 0 | 0 |
| 26 | 0 | 0 | 0 | 0 | 0 |
| 27 | 0 | 0 | 0 | 0 | 0 |
| 28 | 0 | 0 | 0 | 0 | 0 |
| 29 | 19 | 18 | 0 | 0 | 0 |
| 32 | 0 | 0 | 0 | 0 | 0 |
| Comparative Agents zinc ethylene-bis-dithiocarbamate | 78 | 36 | 81 | 50 | 55 |
| Control | 100 | 100 | 100 | 100 | 100 |

The superior fungicidal action as against the known comparative agents is clearly to be seen from the above results.

EXAMPLE 8

The products as 20% powder preparations were homogeneously admixed with a compost soil heavily infested by root gall nematodes. Without a waiting period, 20 cucumber seeds per concentration were seeded. After a cultivation time of 30 days at a temperature of 23°–25° C., the nematocidal action was evaluated by counting the root galls formed in the waterbath. The following table states the reduction of attack in percent. In the control, an average of 90 root galls per seedling had formed.

| Compound No. | Active substance per liter of soil | Nematocidal action in % (Meloidogyne incognita) |
|---|---|---|
| 3 | 40 mg | 100% |
|  | 60 mg | 100% |
| 4 | 40 mg | 96% |
|  | 60 mg | 99% |
| 5 | 40 mg | 90% |
|  | 60 mg | 98% |
| 17 | 40 mg | 90% |
|  | 60 mg | 94% |
| 18 | 40 mg | 61% |
|  | 60 mg | 90% |
| 19 | 40 mg | 72% |
|  | 60 mg | 82% |

The findings of this experiment show the nematocidal action of the compounds according to the invention.

EXAMPLE 9

Control of *Pyrenochaeta lycopersici*, corky root disease of the tomato.

On a naturally infested open field area, 2-dichloromethyl-5-methylsulfonyl-1,3,4-thiadiazole was scattered as a 10% granulate formulation and hoed in 20 cm deep. At the time of treatment, the sandy loam had a relative soil moisture of 10%. After a reaction period of 3 weeks, tomato plants of the variety "Ronald-M" which were 8 weeks old were set out at a distance from each other of 50 × 70 cm. The harvest results indicated in the table are average values of 40 plants per lot and refer to harvested ripe tomatoes.

| g of active ingr. per square meter | Yield per plant | Tomatoes per plant | Weight of single tomato |
|---|---|---|---|
| 20 g | 2209 g (213%) | 28 (165%) | 78 g (130%) |
| 10 g | 1774 g (171%) | 27 (159%) | 66 g (110%) |
| 0 g | 1036 g (100%) | 17 (100%) | 60 g (100%) |

EXAMPLE 10

Control of *Thielaviopsis basicola* on tobacco.

A 10% powder preparation of 2-trifluoromethyl-5-methylsulfonyl-1,3,4-thiadiazole was homogeneously admixed to a soil heavily infested by *Thielaviopsis basicola*. After a reaction time of 1 week, tobacco seedlings of the variety *Nicotiana tabacum* var. "White Burley" were set out and cultivated for 5 weeks in the greenhouse at 22°–32° C. The attack and weight of the fresh plant are evident from the table.

| Active ingr. per liter of soil | Attack 0–5 | Weight of fresh plant (leaves and stems | Weight of roots (air-dry) |
|---|---|---|---|
| 20 mg | 0.5 | 115 g | 11 g |
| 30 mg | 0 | 118 g | 11 g |
| 40 mg | 0 | 104 g | 9 g |
| Steamed soil | 0 | 111 g | 12 g |
| Infested soil | 5 | 21 g | 0.5 g |

0 = no attack
1 = very slight attack
2 = slight attack
3 = medium attack
4 = strong attack
5 = very strong attack

EXAMPLE 11

Fungicidal effect of
2-tricluoromethyl-5-methylsulfonyl-1,3,4-thiadiazole (1)
2-trifluoromethyl-5-ethylsulfonyl-1,3,4-thiadiazole (36)
2-trifluoromethyl-5-methylsulfinyl-1,3,4-thiadiazole (35)
2-trifluoromethyl-5-ethylsulfinyl-1,3,4-thiadiazole (36)
in the vapor phase:

Nutrient medium inoculated with nycelium of *Pythium ultimum* or *Rhizoctonia solani* in open Petri dishes was placed in glass vessels 12 cm tall. First the quantity of product as a 10% powder preparation had been placed on the bottom of the glasses. After a reaction time of 3 days (Pythium) and 5 days (Rhizoctonia) at a temperature of 22° C. in the covered glass vessel, the mycelium growth was evaluated. While in the untreated glasses, the Petri dishes were completely grown over with Pythium or Rhizoctonia, the treatments showed no mycelium growth even at a dose of 1 mg of active ingredient per liter.

EXAMPLE 12

Production of a dry disinfectant.

The following constituents are mixed together:

10% by weight of 2-trifluoromethyl-5-methylsulfonyl-1,3,4-thiazole; 87.8% by weight of talcum; 0.2% by weight of new fuchsine; 2% by weight of paraffin oil.

The mixture is then ground in an air jet mill to a finely dispersed powder. This preparation may be used as disinfectant as described above.

What is claimed is:

1. A method for the protection of plants against infestation by fungi which comprises applying to said plants a fungi controlling amount of a compound having the structure:

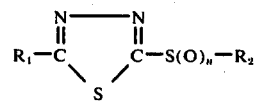

wherein $R_1$ is a lower haloalkyl having from 1 to 7 carbon atoms, $R_2$ is an alkyl group having from 1 to 8 carbons, and $n$ is 1 or 2.

2. The method of claim 1 wherein the compound is applied directly to the growing plants.

3. The method of claim 1 wherein the compound is applied to the seed prior to planting.

4. The method of claim 1 wherein the compound is applied to and admixed with the soil at the time of seed planting.

5. A method according to claim 1 wherein the control of plant fungi is achieved by applying to the plants fungi-controlling amount of said compound in a composition consisting essentially of from about 0.1 to about 80 weight percent of said compound, the balance being a carrier for said compound.

6. A method according to claim 1 wherein the compound is 2-trifluoromethyl-5-methylsulfonyl-1,3,4-thiadiazole.

7. The method of claim 1 wherein $R_1$ is selected from the group consisting of chloromethyl, dichloromethyl, trichloromethyl, bromomethyl, and triflouromethyl.

* * * * *